(12) United States Patent
Quinn

(10) Patent No.: US 9,656,027 B2
(45) Date of Patent: May 23, 2017

(54) SINGLE-USE INJECTOR OF LOW COST

(75) Inventor: Michael Quinn, East Hanover, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 640 days.

(21) Appl. No.: 14/117,846

(22) PCT Filed: May 18, 2011

(86) PCT No.: PCT/US2011/000876
§ 371 (c)(1),
(2), (4) Date: Nov. 14, 2013

(87) PCT Pub. No.: WO2012/158135
PCT Pub. Date: Nov. 22, 2012

(65) Prior Publication Data
US 2014/0088512 A1    Mar. 27, 2014

(51) Int. Cl.
*A61M 5/32* (2006.01)
*A61M 5/28* (2006.01)
(Continued)

(52) U.S. Cl.
CPC .......... *A61M 5/3271* (2013.01); *A61M 5/282* (2013.01); *A61M 5/283* (2013.01);
(Continued)

(58) Field of Classification Search
CPC ........ A61M 5/24; A61M 5/282; A61M 5/283; A61M 5/3243; A61M 5/3257; A61M 5/326; A61M 5/3271; A61M 5/3272
See application file for complete search history.

(56) References Cited

U.S. PATENT DOCUMENTS

| 3,500,830 A | 3/1970 | Eck |
| 4,883,473 A | 11/1989 | Thomas |

(Continued)

FOREIGN PATENT DOCUMENTS

| FR | 2439020 | 5/1980 |
| GB | 989185 | 4/1965 |

(Continued)

*Primary Examiner* — Laura Bouchelle
(74) *Attorney, Agent, or Firm* — Dickinson Wright PLLC

(57) ABSTRACT

An injection device (100, 200), including a safety shield (104, 204) and a housing (108, 208). The safety shield (104, 204) has a first end and a surface disposed at a second end thereof for contacting a patient's skin, and a shield tab (164, -240) extending therefrom. The housing (108, 208) is slidably disposed with respect to the safety shield (104, 204) and includes a guide groove (172, 252) for engaging the shield tab (164, 240) to guide movement of the housing (108, 208) relative to the safety shield (104, 204). The guide groove (172, 252) has first (184, 256) and second (188, 260) axial portions and a substantially helical portion (192, 264) connecting the first and second axial portions (184,188, 256, 260). The device (100, 200) also includes a medicament container (120, 220) connected with the housing (108, 208) and having a needle (124, 224) affixed thereto in communication with a medicament disposed within the medicament container (120, 220). The medicament container (120, 220) is displaceable relative to the safety shield (104, 204) from an initial position to an injection position, to a withdrawn position.

17 Claims, 12 Drawing Sheets

(51) Int. Cl.
*A61M 5/46* (2006.01)
*A61M 5/24* (2006.01)

(52) U.S. Cl.
CPC ............ *A61M 5/288* (2013.01); *A61M 5/326* (2013.01); *A61M 5/3272* (2013.01); *A61M 5/3287* (2013.01); *A61M 5/46* (2013.01); *A61M 2005/2474* (2013.01); *A61M 2005/3247* (2013.01); *A61M 2005/3267* (2013.01)

(56) References Cited

U.S. PATENT DOCUMENTS

| | | | |
|---|---|---|---|
| 4,955,871 A | 9/1990 | Thomas | |
| 5,295,965 A | 3/1994 | Wilmot | |
| 5,599,309 A | 2/1997 | Marshall et al. | |
| 5,634,906 A | 6/1997 | Haber et al. | |
| 5,688,241 A * | 11/1997 | Asbaghi ............... | A61M 5/326 604/110 |
| 5,984,899 A | 11/1999 | D'Alessio et al. | |
| 6,183,446 B1 | 2/2001 | Jeanbourquin | |
| 6,569,115 B1 | 5/2003 | Barker et al. | |
| 7,462,168 B2 * | 12/2008 | Stonehouse ........... | A61M 5/326 604/192 |
| 7,645,265 B2 | 1/2010 | Stamp | |
| 7,670,314 B2 | 3/2010 | Wall et al. | |
| 7,981,085 B2 | 7/2011 | Ethelfeld | |
| 2003/0212362 A1 | 11/2003 | Roser | |
| 2008/0228143 A1 | 9/2008 | Stamp | |
| 2009/0024093 A1 * | 1/2009 | Carrel et al. ......... | A61M 5/326 604/198 |
| 2010/0268170 A1 * | 10/2010 | Carrel ................. | A61M 5/2033 604/198 |

FOREIGN PATENT DOCUMENTS

| | | |
|---|---|---|
| JP | H07503384 A | 4/1995 |
| JP | 8-505543 | 6/1996 |
| JP | 2000-512523 A | 9/2000 |
| JP | 2004-537376 A | 12/2004 |
| JP | 2005-500871 A | 1/2005 |
| JP | 2007-518507 | 7/2007 |
| JP | 2010-540059 A | 12/2010 |
| WO | 2009040602 A1 | 4/2009 |
| WO | WO2010035056 A1 | 4/2010 |

* cited by examiner

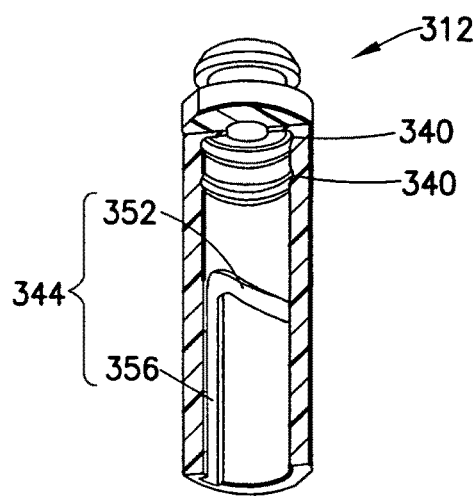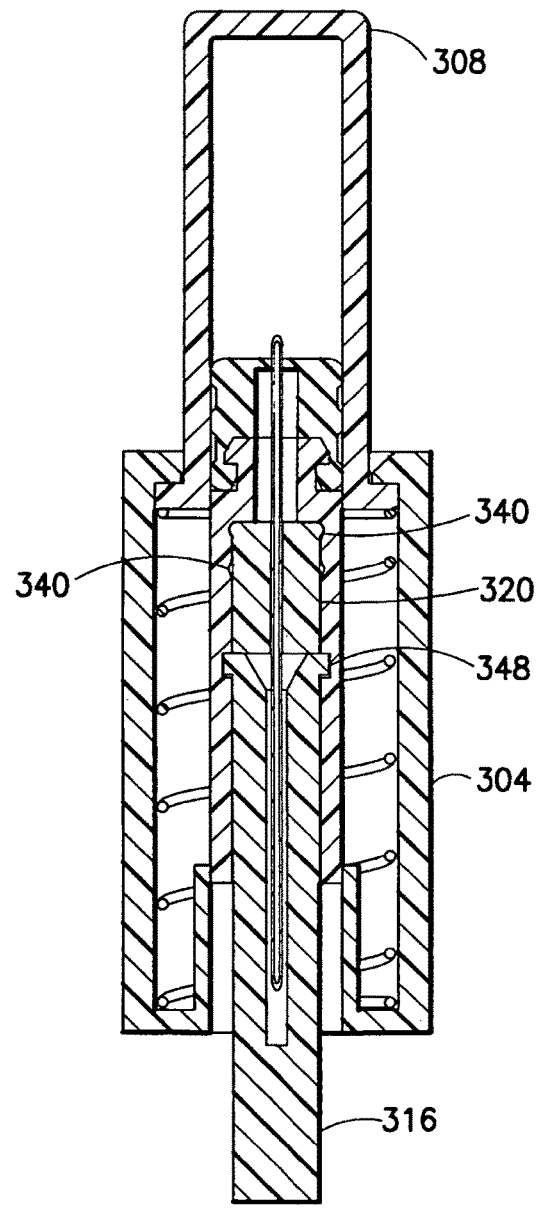
FIG.19
FIG.20

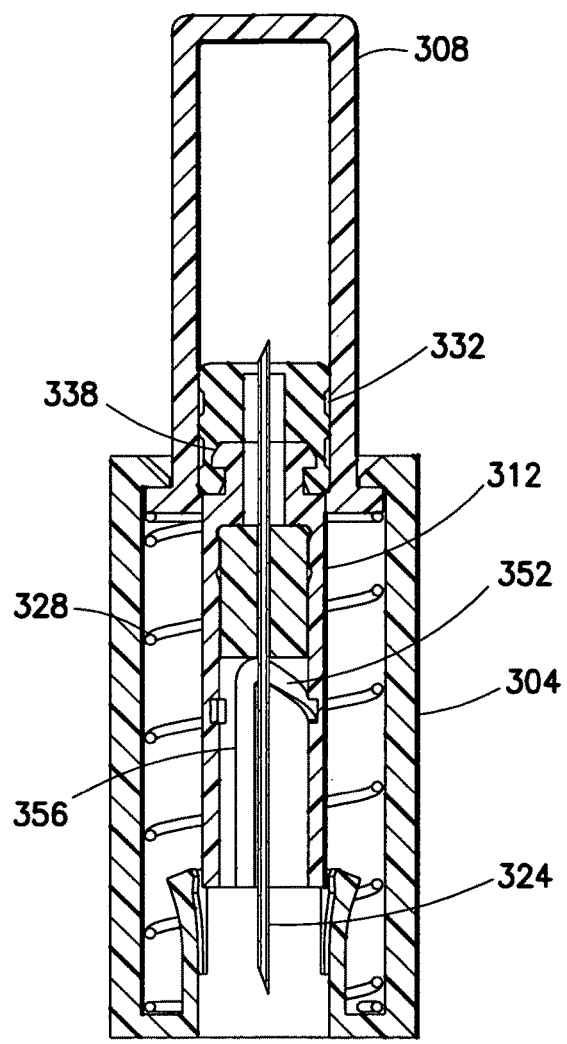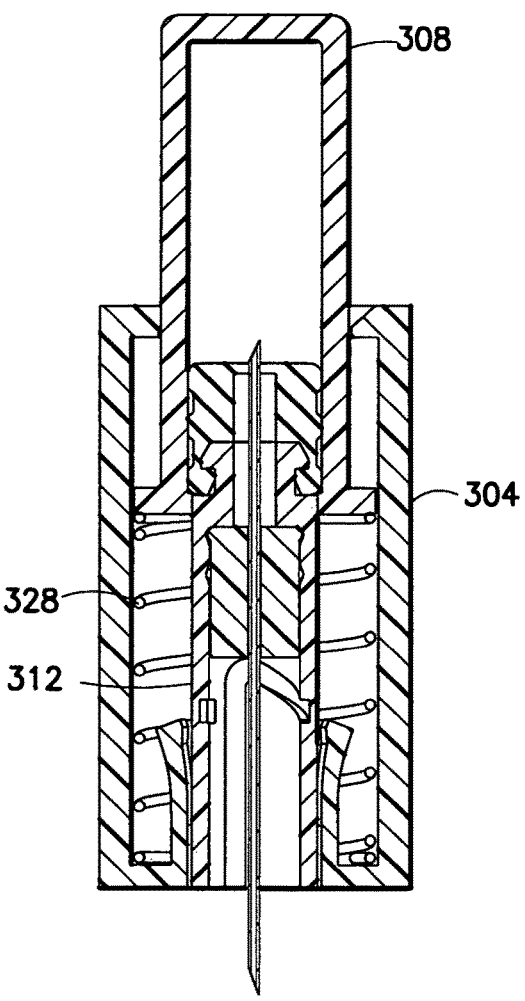
FIG.21
FIG.22

SINGLE-USE INJECTOR OF LOW COST

FIELD OF THE INVENTION

The present invention relates generally to an injection device for dispensing a medicament, and more particularly to a low-cost, single-use injection device.

BACKGROUND OF THE INVENTION

Various injection devices are known in the art. Many such injection devices, however, require medical training for proper use. In addition, many such injection devices are expensive. Thus, there is a need to provide a low-cost, intuitive injection device that can be properly used by untrained or minimally trained people for self-injection or injection of others. For example, such a needed device could be used for inoculations in developing areas of the world where medical care is difficult to obtain, or for a parent to inoculate a child. In addition, needles may be intimidating to some patients. Accordingly, it is desirable for an injection device to hide the needle from the user, both before and after the injection.

SUMMARY OF THE INVENTION

An aspect of the present invention is to provide a low-cost, single-use injection device. Another aspect of the present invention is to provide an intuitive injection device that can be properly used by untrained or minimally trained people for self-injection or injection of others. Yet another aspect of the present invention is to provide an injection device in which the needle is hidden prior to injection and shielded subsequent to injection.

The foregoing and/or other aspects of the present invention are achieved by providing an injection device, including a safety shield and a housing. The safety shield has a first end and a surface disposed at a second end thereof for contacting a patient's skin, and a shield tab extending therefrom. The housing is slidably disposed with respect to the safety shield and includes a guide groove for engaging the shield tab to guide movement of the housing relative to the safety shield. The guide groove has first and second axial portions and a substantially helical portion connecting the first and second axial portions. The device also includes a medicament container connected with the housing and having a needle affixed thereto in communication with a medicament disposed within the medicament container. The medicament container is displaceable relative to the safety shield from an initial position to an injection position, to a withdrawn position. The device additionally includes a biasing member biasing the medicament container away from the safety shield and an injector member slidably disposed relative to the medicament container, for expelling the medicament from the medicament container.

The foregoing and/or other aspects of the present invention are also achieved by providing an injection device, including a safety shield having a first end and a surface disposed at a second end thereof for contacting a patient's skin, and a medicament container slidably connected to the safety shield. The medicament container includes a needle affixed thereto in communication with a medicament disposed within the medicament container. The medicament container is displaceable relative to the safety shield from an initial position to an injection position, to a withdrawn position. The device also includes an injector member having a plunger and a stopper disposed at a first end of the plunger, a biasing member biasing the medicament container away from the safety shield, and a housing slidably disposed with respect to both the safety shield and the medicament container. The housing includes a cantilevered upper locking arm selectively preventing displacement of the housing and the plunger relative to the medicament container. One of the upper locking arm and the safety shield includes a ramp and the remaining one of the upper locking arm and the safety shield includes a corresponding radial protrusion. Upon displacement of the medicament container from the initial position to the injection position in which the needle extends beyond the safety shield, the ramp contacts the radial protrusion to radially displace a free end of the upper locking arm, to permit movement of the housing relative to the medicament container.

The foregoing and/or other aspects of the present invention are also achieved by providing a an injection device, including a safety shield having a surface for contacting a patient's skin, an inner housing slidably connected to the safety shield and having a cam track with first and second portions, a needle hub slidably connected to the inner housing to move from a first position to a second position relative thereto, and a double-ended needle affixed to the needle hub. The device also includes a medicament container for holding a medicament, slidably connected to the safety shield, a stopper slidably disposed in the medicament container, a biasing member disposed within the safety shield and biasing the medicament container in a first direction, and a needle shield for selectively covering a first end of the needle, the needle shield having at least one cam tab slidably engaged with the cam track. Displacement of the cam tab along the first portion of the cam track displaces the needle hub to the second position, piercing the stopper with the needle.

Additional and/or other aspects and advantages of the present invention will be set forth in part in the description that follows and, in part, will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, in which:

FIG. 19 is a partial cross-sectional view of an inner housing of the device of FIG. 17;

FIG. 20 is a cross-sectional view of the device of FIG. 17 with a needle-pierced stopper;

FIG. 21 is a cross-sectional view of the device of FIG. 17 with a needle shield removed;

FIG. 22 is a cross-sectional view of the device of FIG. 17 with the needle deployed;

DETAILED DESCRIPTION OF EXEMPLARY EMBODIMENTS

Figure 2:
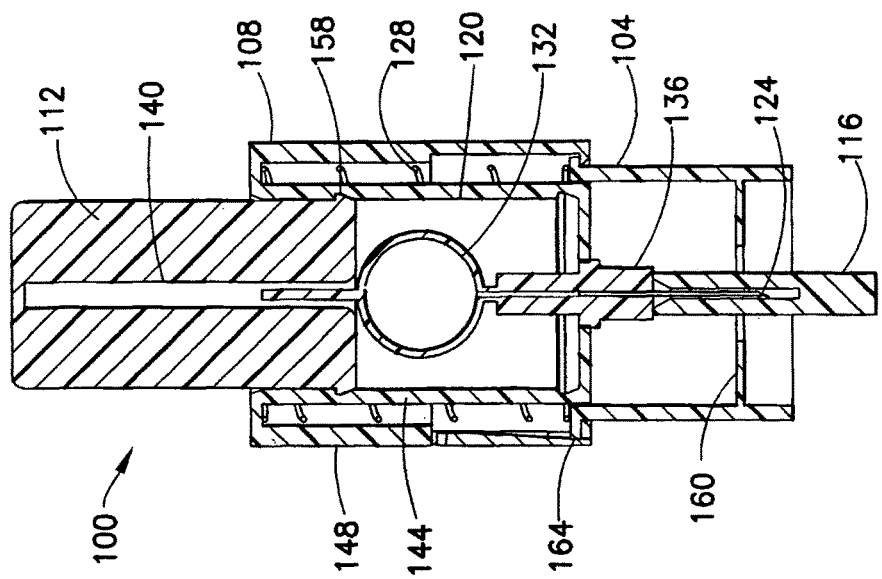
FIG. 2 is a cross-sectional view of the device of FIG. 1 in an initial state.

Reference will now be made in detail to embodiments of the present invention, examples of which are illustrated in the accompanying drawings, wherein like reference numerals refer to the like elements throughout. The descriptions of these embodiments exemplify the present invention by referring to the drawings.

Figure 1:
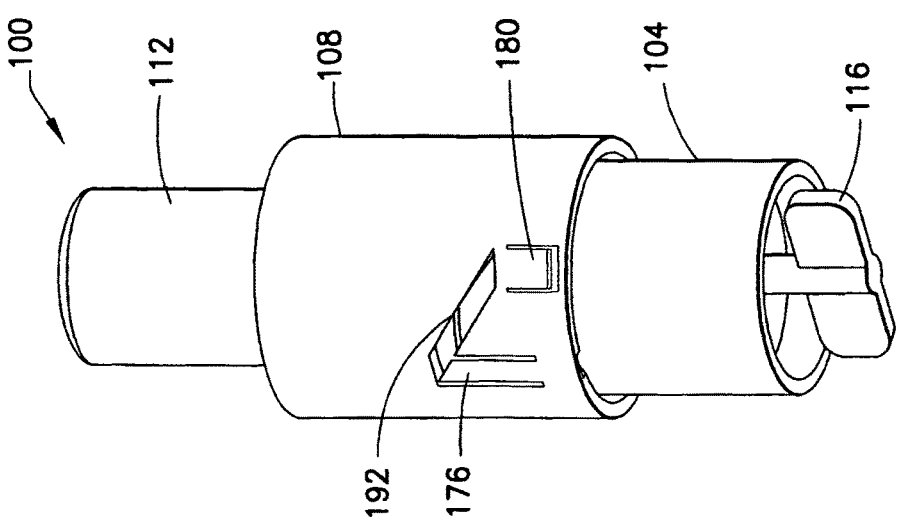
FIG. 1 is a perspective view of an injection device in accordance with an embodiment of the present invention.

FIG. 1 is a perspective view of an injection device 100 in accordance with an embodiment of the present invention. The injection device 100 includes a safety shield 104, a housing 108, and an injector member or injector button 112. The housing 108 is slidably connected with the safety shield 104. The injection device 100 also includes a removable needle shield 116.

FIG. 2 is a cross-sectional view illustrating the injection device 100 in an initial state. As shown in FIG. 2, injection device 100 also includes a medicament container 120 with the needle 124 fixed thereto and a biasing member 128, such as a spring 128. According to one embodiment, the medicament container 120 includes a flexible blister 132 with a hub 136 for holding the needle 124. The needle 124 is in fluid connection with the flexible blister 132 via the hub 136. An example of such a medicament container is disclosed in U.S. Pat. No. 4,955,871 to Thomas, which is incorporated herein by reference in its entirety. According to one embodiment, the medicament container 120 is fixedly connected with the housing 108. According to another embodiment (not shown), the medicament container includes a double ended needle that punctures a valve membrane when the needle shield is pushed rearward. This configuration acts as an anti-tamper, anti-re-use feature.

FIG. 2 also illustrates that the injector button 112 includes an internal slot 140 axially aligned with the flexible blister 132. In addition, FIG. 2 illustrates that the housing 108 includes inner and outer walls 144 and 148. The biasing member 128 is disposed between the inner and outer walls 144 and 148 and the injector button 112 and the medicament container 120 are disposed radially within the inner wall 144. The injector button 112 is slidably disposed relative to the medicament container 120 and the inner wall 144.

The inner wall 144 has a pair of detents, including an initial detent 152 and a locking detent 156. According to one embodiment, the detents 152 and 156 are circumferential recesses on an interior surface of the inner wall 144. According to another embodiment, the detents 152 and 156 are discontinuous circumferential recesses disposed on the interior surface of the inner wall 144. The injector button 112 includes a button projection 158 disposed at a distal end thereof and having a shape corresponding to the detents 152 and 156. The button projection 158 and the initial detent 152 interact to prevent proximal movement of the injector button 112 relative to the housing 108 subsequent to the button projection 158 engaging the initial detent 152. Similarly, as discussed in greater detail below, the button projection 158 and the locking detent 156 interact to prevent proximal movement of the injector button 112 relative to the housing 108 subsequent to the button projection 158 engaging the locking detent 156.

Figure 3:
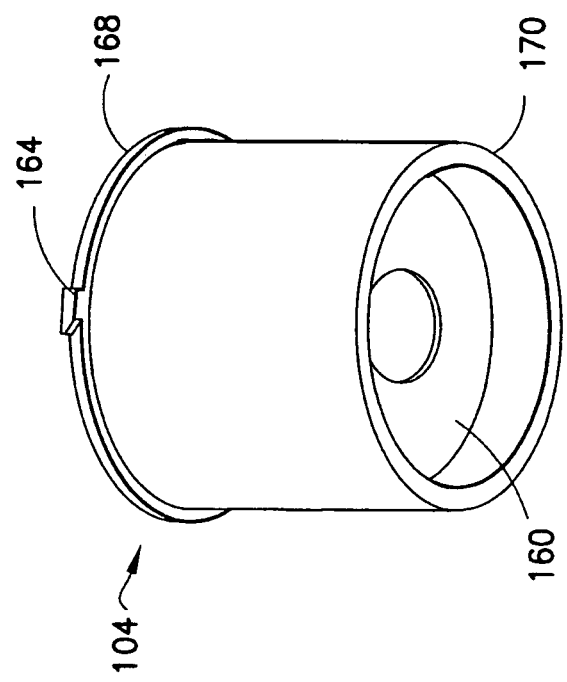
FIG. 3 is a perspective view of a safety shield of the device of FIG. 1.

As shown in FIGS. 2 and 3, the safety shield 104 is substantially cylindrical and has a depth stop 160 for limiting penetration of the needle 124 into a patient's skin. The safety shield 104 also includes a shield tab 164 radially projecting from a flange 168 disposed at a proximal end of the safety shield 104. The flange 168 provides a bearing surface for a distal end of the biasing member 128 and the shield tab 164 interacts with a guide groove 172 in the housing 108 to guide movement of the housing 108 relative to the safety shield 104. The distal end of the safety shield 104 defines a surface 170 for contacting a patient's skin.

Figure 4:
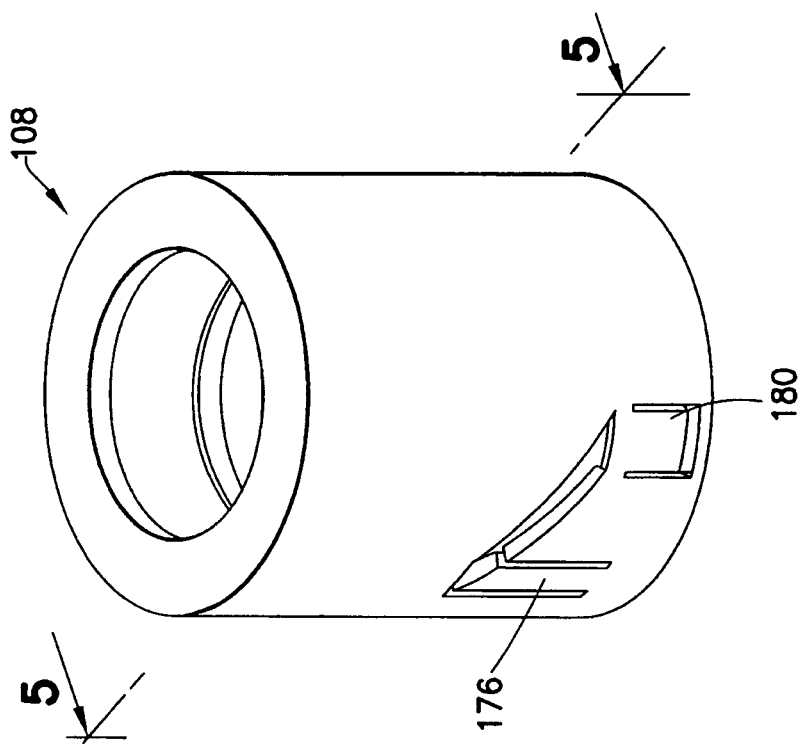
FIG. 4 is a perspective view of a housing of the device of FIG. 1.
Figure 5:
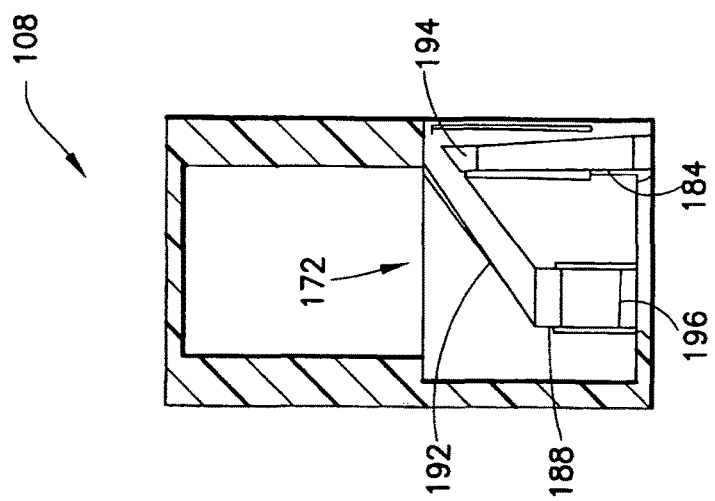
FIG. 5 is a cross-sectional view of the housing of FIG. 4 taken along line 5-5 of FIG. 4.

As shown in FIG. 4, the housing 108 includes a cantilevered upper flexible arm 176 and a cantilevered lower flexible arm 180. As described in greater detail below, the upper flexible arm 176 and the lower flexible arm 180 are locking members of the guide groove 172. FIG. 5 is a cross-sectional view of the housing 108 taken along line 5-5 of FIG. 4. As shown in FIG. 5, the guide groove 172 includes first and second substantially axial portions 184 and 188 and a substantially helical portion 192 connecting the first and second axial portions 184 and 188. According to one embodiment, for molding purposes, the substantially helical portion 192 cuts through the housing 108. As discussed in greater detail below, also shown in FIG. 5, the upper flexible arm 176 includes a ramp 194 disposed at the free end of an internal side thereof. Additionally, the lower flexible arm 180 includes a ramp hook 196.

Figure 6:
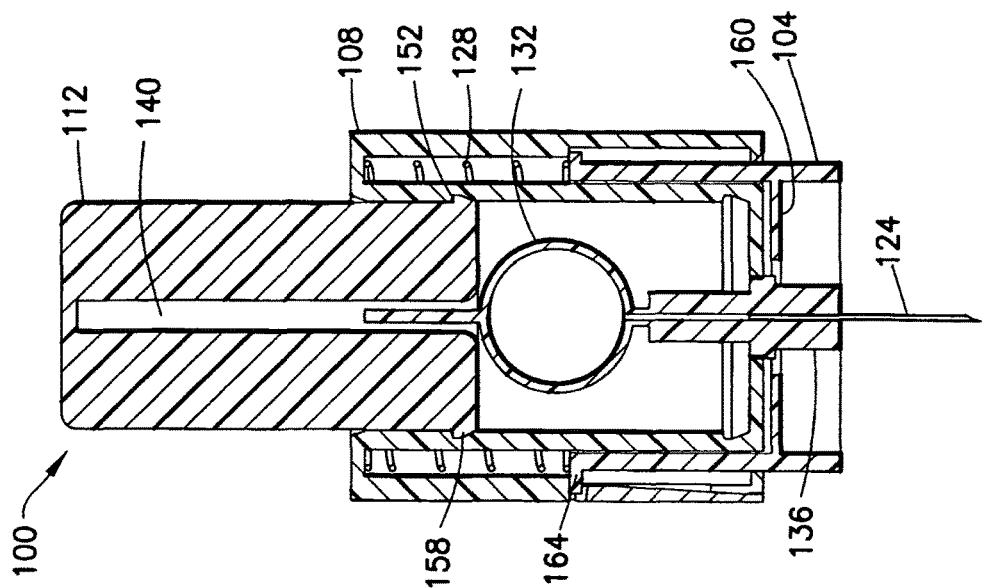
FIGS. 6-8 are cross-sectional views illustrating operation of the device of FIG. 1.
Figure 8:
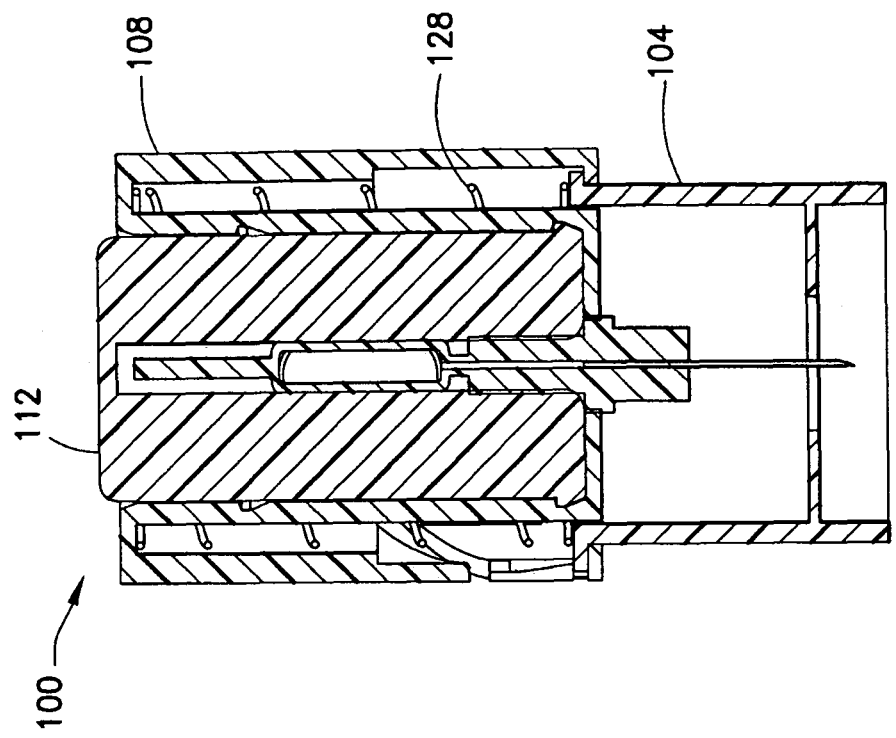
Figure 7:
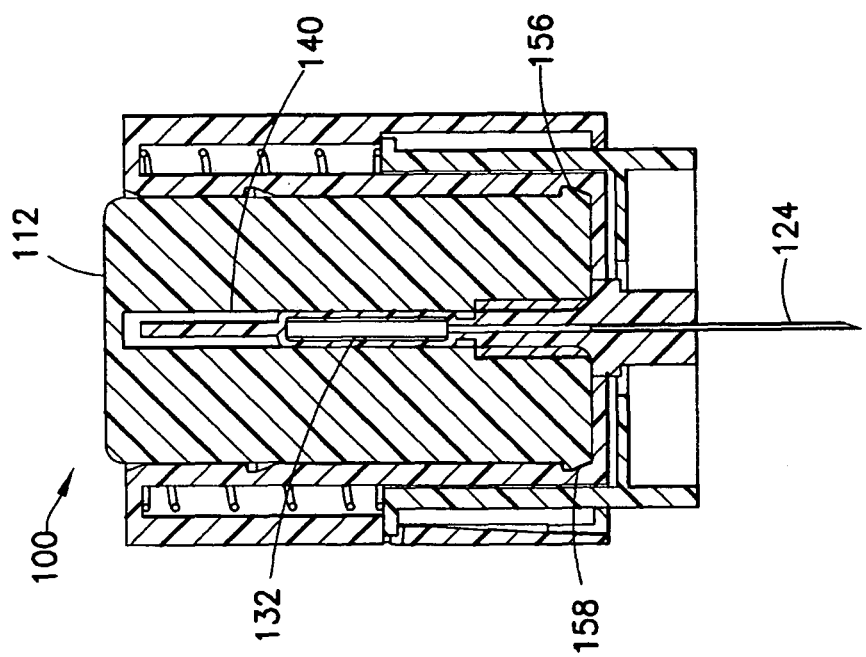

FIGS. 6-8 are cross-sectional views illustrating operation of the injection device 100. To operate the device, a user first removes the needle shield 116 and places the surface 170 of the safety shield 104 on a patient's skin 194. Subsequently, the user depresses the injector button 112 to displace the medicament container to an injection position. The force required to compress the biasing member 128 and the force required to penetrate the user's skin with the needle 124 are less than that required to displace the button projection 158 from the initial detent 152. Accordingly, when the user depresses the injector button 112, the housing 108 slides distally relative to the safety shield 104 and the needle 124 penetrates the user's skin 198, stopping at a predetermined depth when the hub 136 of the medicament container 120 contacts the depth stop 160, as shown in FIG. 6.

During this distal displacement of the housing 108 relative to the safety shield 104, the shield tab 164 engages the first axial portion 184 of the guide groove 172 and travels proximally relative thereto. In other words, the engagement of the shield tab 164 and the first axial portion 184 constrains the displacement of the housing 108 relative to the safety shield 104 to be axial and prevents rotation of the housing 108 relative to the safety shield 104. As the hub 136 nears the depth stop 160, the shield tab 164 passes the ramp 194 and radially displaces the free end of the upper flexible arm 176. As the hub 136 engages the depth stop 160, the shield tab 164 completes passing the ramp 194 and reaches the proximal end of the first axial portion 184. After the shield tab 164 passes the ramp 194, the free end of the upper flexible arm 176 snaps back to form a portion of the helical portion 192 of the guide groove 172 and to prevent subsequent axial movement of the shield tab 164 in the first axial portion 184.

Turning to FIG. 7, as the user continues to depress the injector button 112, the button projection 158 displaces from the initial detent 152 and the injector button 112 displaces distally relative to the inner wall 144 and the medicament container 120 until the button projection 158 engages the locking detent 156. During this distal displacement of the injector button, the walls of the internal slot 140 engage and compress the flexible blister 132 and expel the medicament from the flexible blister 132 into the patient. Once the button projection 158 engages the locking detent 156 (defining an injection state), the corresponding shapes thereof prevent subsequent proximal displacement of the injector button 112 relative to the housing 108. In addition, once the medicament is injected, the proximal end of the injector button 112 is disposed sufficiently close to the proximal end of the housing 108 that a user cannot gain a purchase on the injector button 112 to attempt proximal displacement of the injector button 112. According to one embodiment, once the medicament is injected, the proximal end of the injector button 112 is substantially flush with the proximal end of the housing 108.

Figure 9:
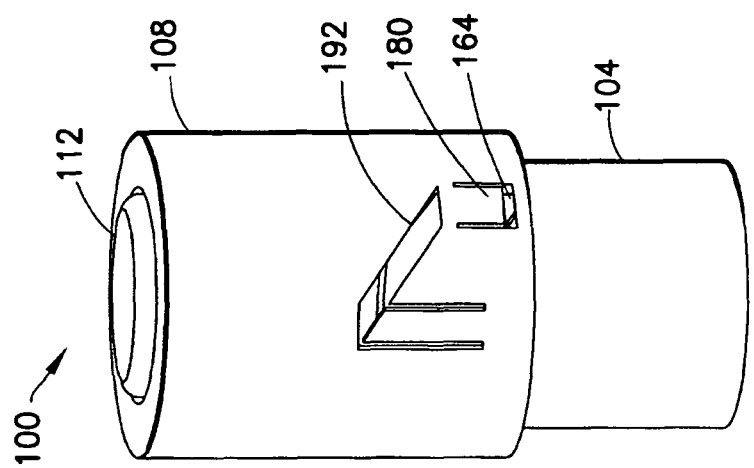
FIG. 9 is a perspective view of the device of FIG. 1 in a post-injection safe state.

Subsequent to the injection of the medicament, the user releases the injector button 112 and the biasing member 128 proximally displaces the housing 108 (as well as the medicament container 120 and the injector button 112) relative to the safety shield 104, thereby displacing the medicament container 120 (and the needle 124) to a withdrawn position. Because the shield tab 164 engages the helical portion 192 of the guide groove 172, the during a first portion of the proximal displacement, the housing 108 rotates until the shield tab 164 reaches the proximal end of the second axial portion 188. At this point, the biasing member 128 continues to proximally displace the housing 108 and the engagement of the shield tab 164 in the second axial portion 188 constrains the proximal displacement to be axial. As the housing 108 nears completion of its proximal displacement, the shield tab 164 passes the ramp hook 196 of the lower flexible arm 180 and radially displaces the free end of the lower flexible arm 180. And as the housing 108 completes its proximal displacement (shown in FIGS. 8 and 9), the shield tab 164 completes passing the ramp hook 196 and reaches the distal end of the second axial portion 188. After the shield tab 164 passes the ramp hook 196, the free end of the lower flexible arm 180 snaps back to prevent subsequent axial movement of the shield tab 164 in the second axial portion 188. In other words, the free end of the lower flexible arm 180 locks the shield tab 164 and prevents subsequent displacement of the housing 108 relative to the safety shield 104, thereby fixing the injection device 100 in a post-injection safe state.

Figure 10:
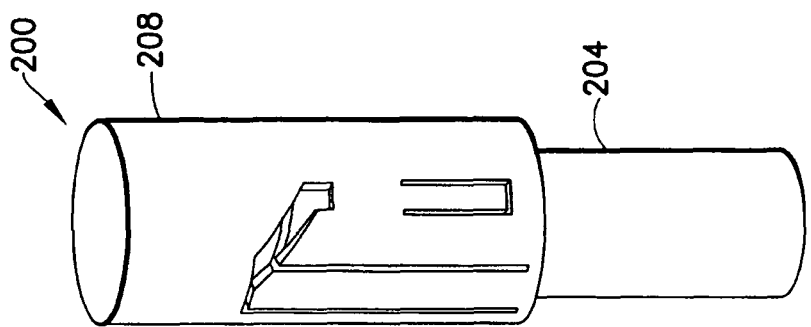
FIG. 10 is a perspective view of an injection device in accordance with another embodiment of the present invention.
Figure 11:
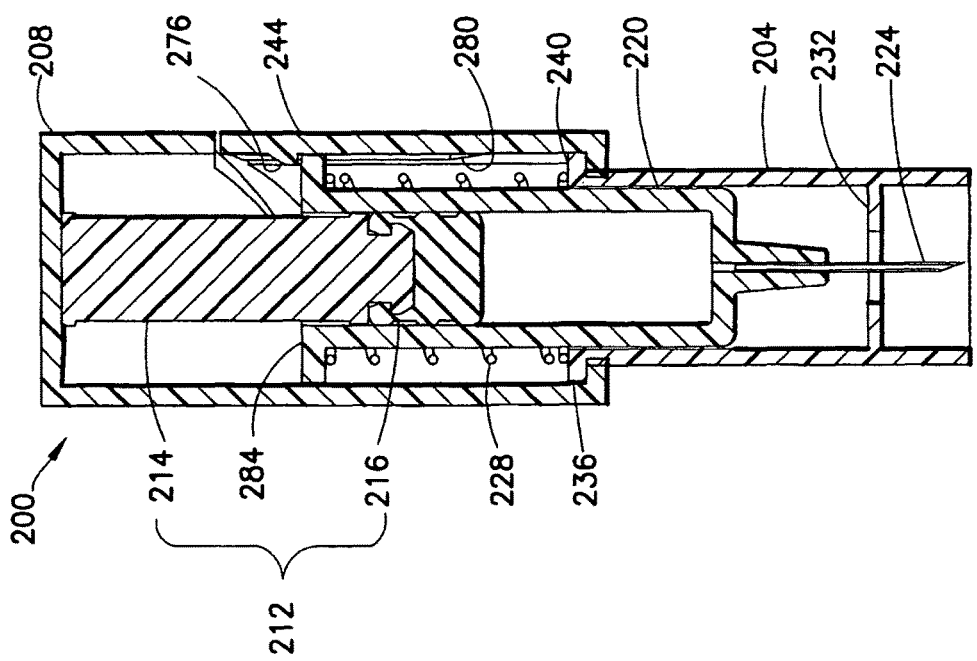
FIG. 11 is a cross sectional view of the device of FIG. 10 in an initial state.
Figure 16:
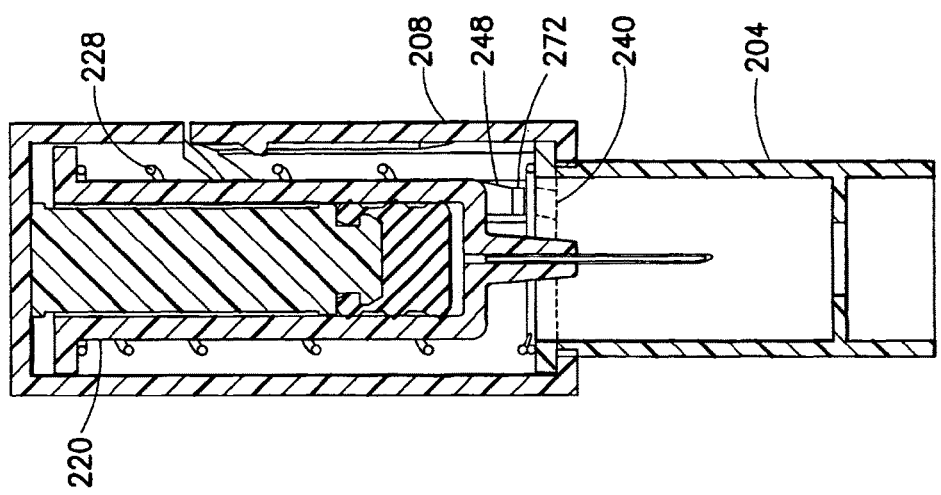
FIG. 16 is a cross-sectional view of the device of FIG. 10 in a post-injection safe state.

FIG. 10 is a perspective view of an injection device 200 in accordance with another embodiment of the present invention and FIG. 11 is a cross sectional view of the injection device 200. As shown in FIG. 10, the injection device 200 includes a safety shield 204 and a housing 208. Although not illustrated, the injection device 200 also includes a removable needle shield. The housing 208 slidably connects to the safety shield 204. As shown in FIG. 11, the injection device 200 also includes an injector member 212 (including a plunger 214 and a stopper 216) that slidably connects with a medicament container 220, which has a needle 224 affixed to a distal end thereof. Further, the injection device 200 includes a biasing member 228 biasing the medicament container 220 proximally away from the safety shield 204. The needle 224 communicates with a medicament disposed within the medicament container 220. Like the medicament container 120, the medicament container 220 is displaceable relative to the safety shield 204 from an initial position (shown in FIG. 11), to an injection position (shown in FIG. 14), to a withdrawn position (shown in FIG. 16). In addition, the safety shield 204 (having a depth stop 232, a flange 236, and a shield tab 240) is substantially similar to the safety shield 104 described previously. Accordingly, further detailed description of the safety shield is omitted for brevity.

Figure 12:
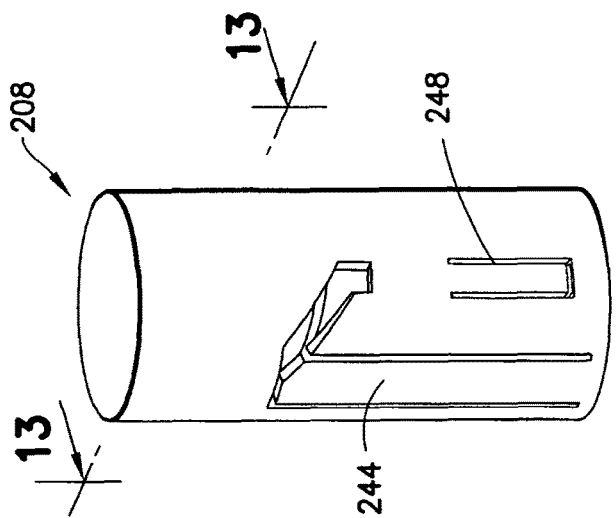
FIG. 12 is a perspective view of a housing of the device of FIG. 10.
Figure 13:
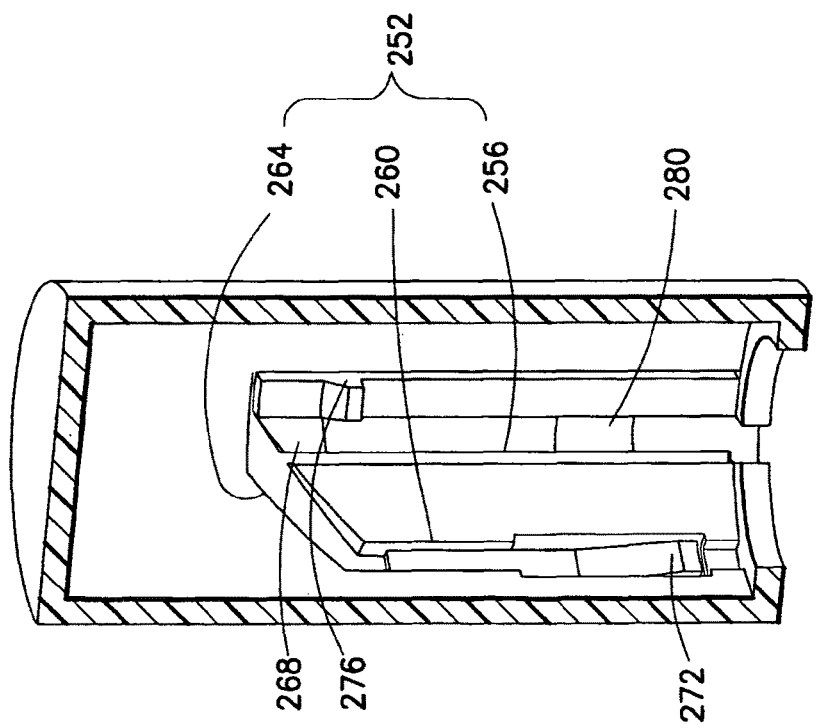
FIG. 13 is a cross-sectional view of the housing taken along line 13-13 of FIG. 12.

FIG. 12 is a perspective view of the housing 208 illustrating that, like the housing 108, the housing 208 includes an upper flexible arm 244 and a lower flexible arm 248. FIG. 13 is a cross-sectional view of the housing 208 taken along line 13-13 of FIG. 12, and illustrates that, also like the housing 108, the housing 208 includes a guide groove 252 that includes first and second axial portions 256 and 260, and a substantially helical portion 264 connecting the first and second axial portions 256 and 260. Additionally, the upper flexible arm 244 is disposed on the first axial portion 256 and the lower flexible arm 248 is disposed on the second axial portion 260. Further, the upper flexible arm 244 includes a ramp 268 disposed at a free end thereof and the lower flexible arm 248 includes a ramp hook 272 disposed at a free end thereof. The ramp 268 and the ramp hook 272 function substantially similarly to the ramp 194 and ramp 196 described previously. Accordingly, further detailed description of the ramp 268 and the ramp-hook 272 are omitted for brevity.

Unlike the housing 108, however, the upper flexible arm 244 includes a locking protrusion 276 at a proximal end thereof for selectively preventing displacement of the housing 208 and the plunger 214 relative to the medicament container 220. The upper flexible arm 244 also has an unlocking ramp 280 disposed thereon. As described in greater detail below, the unlocking ramp 280 interacts with the shield tab 240 to radially displace the free end of the upper flexible arm 244, to permit movement of the housing 208 relative to the medicament container 220. According to one embodiment, as shown in FIG. 13, the upper flexible arm 244 has two portions. The locking protrusion 276 is disposed on a first portion, and the ramp 268 and the unlocking ramp 280 are disposed on a second portion, which also includes the first axial portion 256 of the guide groove 252.

Referring back to FIG. 11, in the initial state, the locking protrusion 276 engages a radial flange 284 disposed at a proximal end of the medicament container 220. This engagement prevents displacement of the housing 208 and the plunger 214 relative to the medicament container 220. Thus, when a user applies force to the proximal end of the housing 208, the radial flange 284 compresses the biasing member 228, and the housing 208, injector member 212, and the medicament container 220 distally displace as a unit relative to the safety shield 204 until the medicament container 220 reaches the depth stop 232, which is an injection state shown in FIG. 14. This displacement of the medicament container 220 also drives the needle 224 to pierce the patient's skin.

Figure 14:
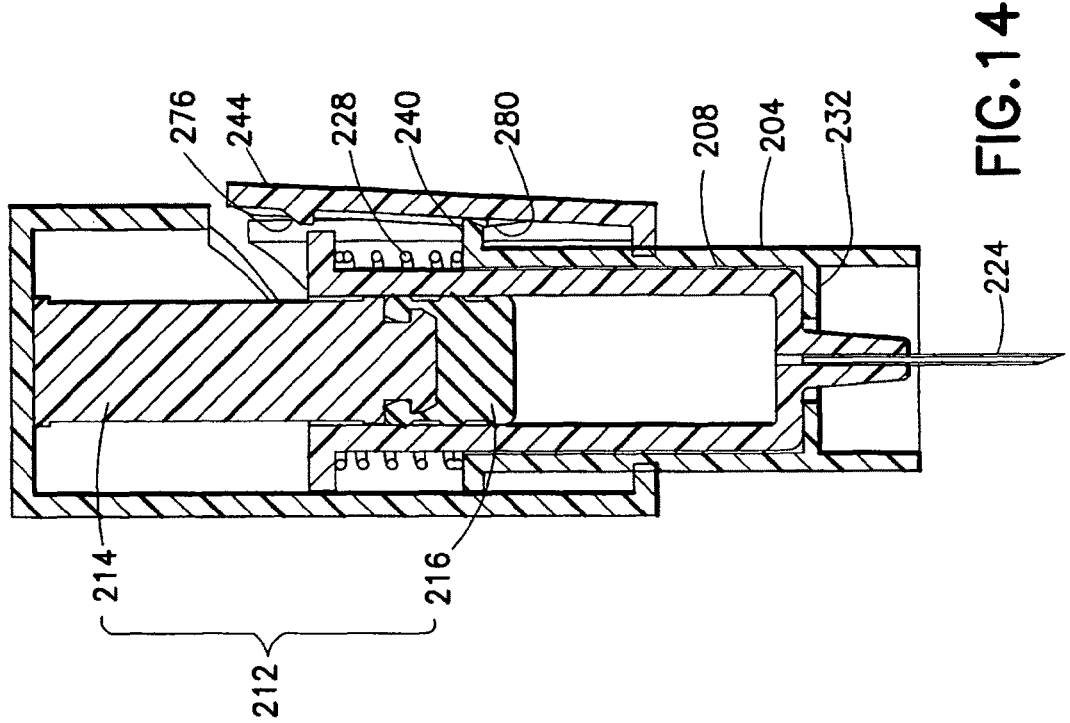
FIG. 14 is a cross sectional view of the device of FIG. 10 in an injection state.
Figure 15:
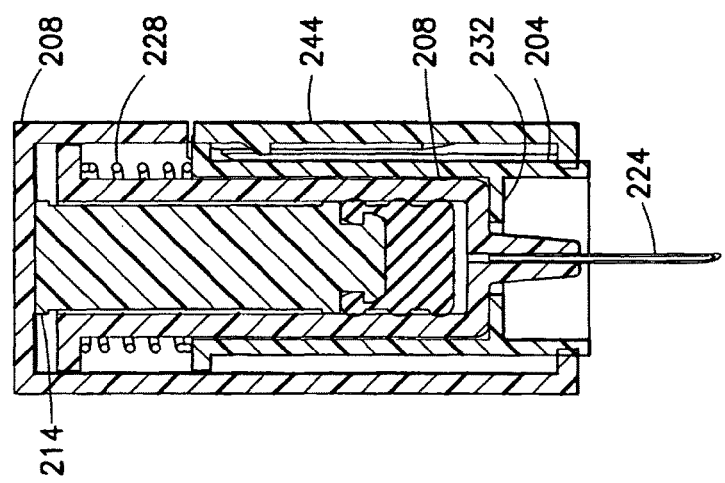
FIG. 15 is a cross-sectional view of the device of FIG. 10 subsequent to injection of a medicament.

As shown in FIG. 14, as the housing 208 and medicament container 220 reach the injection state, the shield tab 240 travels in the first axial portion 256 and engages the unlocking ramp 280 to radially displace a free end of the upper flexible arm 244, thereby disengaging the locking protrusion 276 from the radial flange 284. Accordingly, because the locking protrusion 276 no longer engages the radial flange 284, the housing 208 (as well as the stopper 216 and the plunger 214, which contacts the housing 208) is displaceable relative to the medicament container 220. Thus, as the user continues to apply force to the proximal end of the housing 208, as shown in FIG. 15, the housing 208 and the injector member 212 displace distally relative to the medicament container 220, expelling the medicament from the medicament container 220.

Additionally, during this distal displacement of the housing 208 relative to the safety shield 204, the shield tab 240 continues to travel proximally relative to the first axial portion 256 of the guide groove 252. In other words, the engagement of the shield tab 240 and the first axial portion 256 constrains the displacement of the housing 208 relative to the safety shield 204 to be axial and prevents rotation of the housing 208 relative to the safety shield 204. As the housing approaches the distal end of its stroke and the medicament container 220 nears the depth stop 232, the shield tab 240 passes the ramp 268 and radially displaces the free end of the upper flexible arm 244. And as the medicament container 220 engages the depth stop 232, the shield tab 240 completes passing the ramp 268 and reaches the proximal end of the first axial portion 256. After the shield tab 240 passes the ramp 268, the free end of the upper flexible arm 244 snaps back to form a portion of the helical portion 264 of the guiding groove 252 and to prevent subsequent axial movement of the shield tab 240 in the first axial portion 256.

Similar to the injection device 100 described previously, subsequent to the injection of the medicament, the user releases the housing 208 and the biasing member 228 proximally displaces the housing 208 (as well as the medicament container 220 and the injector member 212) relative to the safety shield 204, thereby displacing the medicament container 220 (and the needle 224) to a withdrawn position. Because the shield tab 240 engages the helical portion 264 of the guide groove 252, during a first portion of the proximal displacement, the housing 208 rotates until the shield tab 240 reaches the proximal end of the second axial portion 260. At this point, the biasing member 228 continues to proximally displace the housing 208 and the engagement of the shield tab 240 in the second axial portion 260 constrains the proximal displacement of the housing 208 to be axial. As the housing 208 nears completion of its proximal displacement, the shield tab 240 passes the ramp hook 272 of the lower flexible arm 248 and radially displaces the free end of the lower flexible arm 248. And as the housing 208 completes its proximal displacement (shown in FIG. 16), the shield tab 240 completes passing the ramp hook 272 and reaches the distal end of the second axial portion 260. After the shield tab 240 passes the ramp hook 272, the free end of the lower flexible arm 248 snaps back to prevent subsequent axial movement of the shield tab 240 in the second axial portion 260. In other words, the free end of the lower flexible arm 248 locks the shield tab 240 and prevents subsequent displacement of the housing 208 relative to the safety shield 204, thereby fixing the injection device 200 in a post-injection safe state.

Figure 17:
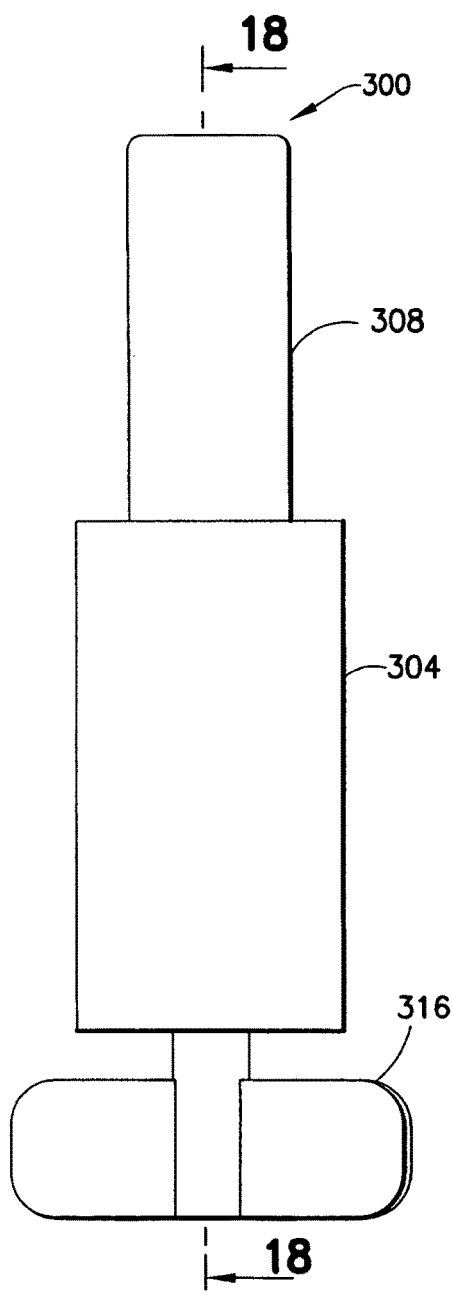
FIG. 17 is a perspective view of an injection device in accordance with another embodiment of the present invention.
Figure 18:
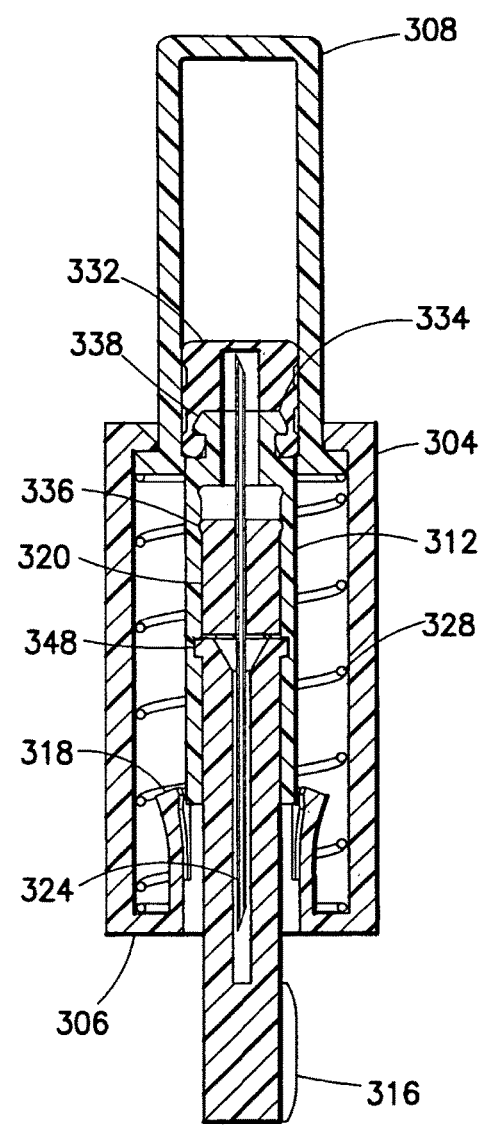
FIG. 18 is a cross-sectional view of the device of FIG. 17 taken along line 18-18 of FIG. 17.

FIG. 17 is a perspective view of an injection device 300 in an initial state and FIG. 18 is a cross-sectional view of the device 300. As shown in FIGS. 17 and 18, the injection device 300 includes a safety shield 304 with a surface 306 for contacting a patient's skin disposed at a distal end thereof, a medicament container 308 slidably connected to the safety shield 304, an inner housing 312 slidably connected to the safety shield 304, and a needle shield 316 for selectively covering a distal end of a needle 324. The medicament container 308 may be made of, for example, glass or plastic. According to one embodiment, the safety shield 304 includes a pair of locking tabs 318, which are biased radially inward. The injection device 300 also includes a needle hub 320 slidably connected to the inner housing 312. The double-ended needle 324 is affixed to the needle hub 320. The injection device 300 further includes a biasing member 328 disposed within the safety shield 304 and proximally biasing the medicament cartridge 308, and a stopper 332 slidably disposed in the medicament cartridge 308. According to one embodiment, the inner housing 312 has a barb 334 at the proximal end thereof engaged with a corresponding recess 338 in the distal end of the stopper 332, to fix the stopper 332 to the inner housing 312.

The needle hub 320 has a radial protrusion 336 disposed at a proximal end thereof and the inner housing 312 includes a pair of detents or receiving grooves 340 (shown in FIG. 19) corresponding to the radial protrusion 336. According to one embodiment, the radial protrusion 336 and the receiving grooves 340 are circumferential. As discussed in greater detail below, the needle hub 320 is movable from a first position, in which the radial protrusion 336 is disposed in a distal one of the receiving groove 340, to a second position, in which the radial protrusion 336 is disposed in a proximal one of the receiving grooves 340.

According to one embodiment, the inner housing 312 also includes a pair of cam tracks 344 that slidably receive a pair of cam tabs 348 of the needle shield 316. As shown in FIG. 19, each cam track 344 includes a first, substantially helical portion 352 and a second, substantially linear portion 356. As the user rotates the needle shield 316, the cam tabs 348 travel along the helical portions 352 until reaching the end of the helical portions 352 (and the beginning of the linear portions 356). This rotation of the needle shield 316 proximally displaces the needle hub 320 from the first position to the second position and pierces the stopper 332 with the proximal end of the needle 324, as shown in FIG. 20.

Subsequently, with the cam tabs 348 disposed in the linear portions 356, the user distally displaces the needle shield 316 to remove it from the injection device 300. The injection device 300, as shown in FIG. 21, is now ready for injection.

Next, the user places the injection device 300 so that the surface 306 of the safety shield 304 contacts the user's skin and presses down on the medicament container 308, compressing the biasing member 328. According to one embodiment, the combination of forces of the back pressure of the medicament in the medicament container 308 and the friction between the stopper 332 and the medicament container 308 is greater than the combination of the force from the biasing member 328 and the force required for the needle 324 to pierce the patient's skin, so that upon distal displacement of the medicament container 308, the needle 324 pierces the patient's skin prior to dispensing of the medicament. This downward pressure on the medicament container 308 drives the needle 324 into the patient's skin until the inner housing 312 contacts the patient's skin, as shown in FIG. 22.

Figure 23:
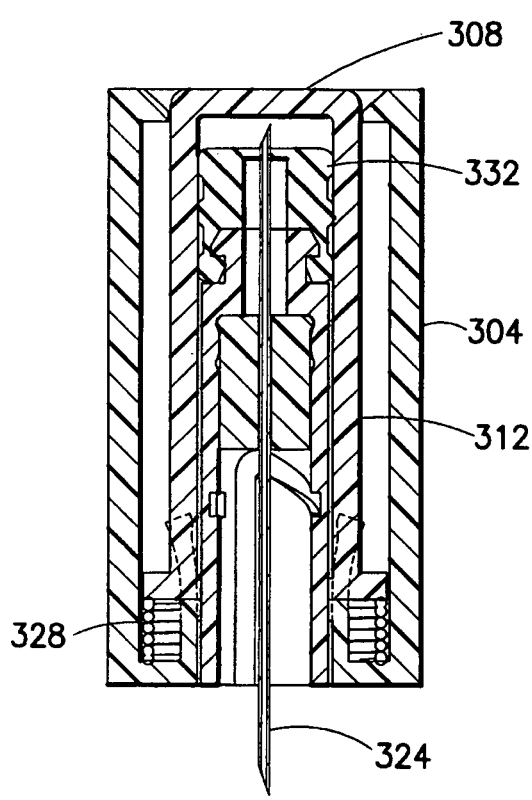
FIG. 23 is a cross-sectional view of the device of FIG. 17 subsequent to injection of a medicament.

Once the inner housing 312 contact the patient's skin, continued downward pressure on the medicament container 308 expels medicament from the medicament container 308 through the needle 324 until the medicament container 308 reaches the end of its stroke, as shown in FIG. 23. According to one embodiment, at the end of the medicament container's stroke, the proximal end of the medicament container 308 is substantially flush with the proximal end of the safety shield 304.

Figure 24:
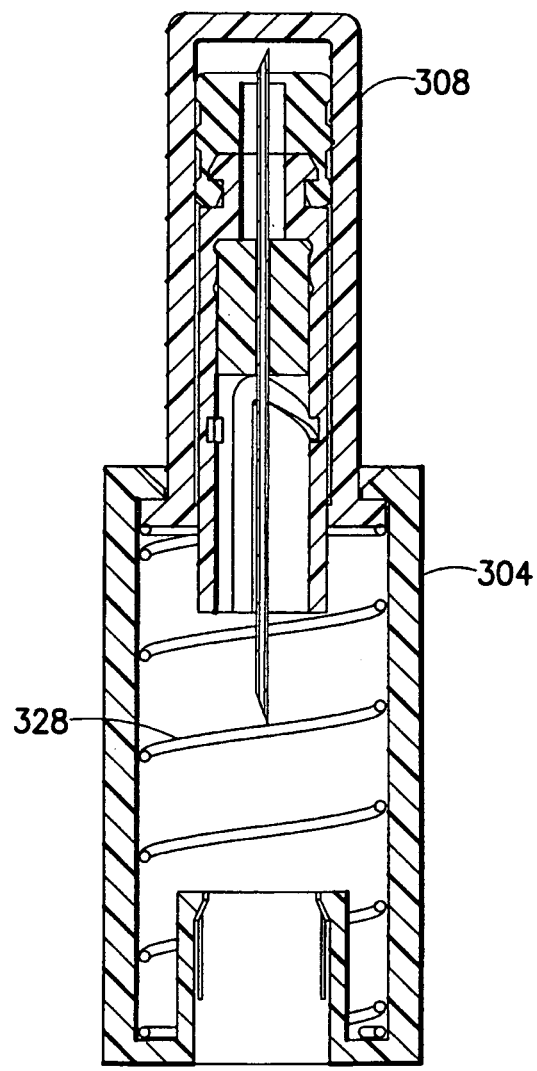
FIG. 24 is a cross-sectional view of the device of FIG. 17 in a post-injection safe state.

Subsequent to the injection of the medicament, the user releases the medicament container 308, and the force of the biasing member 328 proximally displaces the medicament container 308 (as well as the inner housing 312 and the needle 324). Once the distal end of the inner housing 312 passes the locking tabs 318, the locking tabs 318 snap radially inward due to their radially inward bias. In this position, as shown in FIG. 24, the locking tabs 318 prevent subsequent distal displacement of the inner housing 312 therepast, and thus, prevent re-use of the injection device 300.

Embodiments of the present invention are user-friendly, and can hide the needle prior to injection, thereby making it less intimidating to users who might be unaccustomed to injections. Additionally, in embodiments of the present invention, the needle insertion and injection stroke can be achieved in one single motion. Further, the needle can be automatically shielded once the device is removed from the skin in embodiments of the present invention. Moreover, the compact size and low parts count of embodiments of the present invention can reduce manufacturing costs as well as transportation and storage costs.

Compared to traditional autoinjectors, the compact size and low parts count of embodiments of the present invention can be achieved by eliminating some of the higher-order features of such auto injectors. For example, embodiments of the present invention do not require automatic, spring-loaded pushing mechanisms that make an autoinjector "automatic." Instead, users can apply the necessary force. To ensure that users apply a minimum required force and also ensure a swift needle insertion, embodiments of the present invention can have a force-based detent that the user needs to overcome before the injection can begin. Once the detent is overcome, the needle assembly snaps into the skin and then the injection begins. By eliminating the requirement for an automatic, spring-loaded pushing mechanism, other features can also be eliminated, such as an activation button, and a spring-loaded safety device that only allows the injector to be triggered once it is pushed against an object.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of the appended claims and equivalents thereof.

The invention claimed is:

1. An injection device, comprising:
a safety shield having a first end and a surface disposed at a second end thereof for-contacting a patient's skin, the safety shield having a shield tab extending therefrom;
a housing slidably disposed with respect to the safety shield, the housing including a guide groove for engaging the shield tab to guide movement of the housing relative to the safety shield, the guide groove having first and second axial portions and a substantially helical portion connecting the first and second axial portions;
a medicament container connected with the housing and having a needle affixed thereto in communication with a medicament disposed within the medicament container, wherein the medicament container is displaceable relative to the safety shield from an initial position to an injection position, to a withdrawn position;
a biasing member biasing the medicament container away from the safety shield; and
an injector member slidably disposed relative to the medicament container, for expelling the medicament from the medicament container;
wherein:
the medicament container is fixedly connected with the housing;
the housing includes an inner wall and an outer wall;
the biasing member is disposed between the inner and outer walls;
the medicament container is disposed radially inward of the inner wall;
one of the injector member and the inner wall has a radial protrusion and the remaining one of the injector member and the inner wall has a pair of grooves for selectively retaining the radial protrusion and preventing proximal translation of the injector member therepast; and
a first one of the pair of grooves corresponds to an initial state and the remaining one of the pair of grooves correspond to an injected state.

2. The injection device according to claim 1, wherein the safety shield includes a depth stop for limiting penetration of the needle into a patient's skin.

3. The injection device according to claim 1, wherein the housing comprises a cantilevered upper flexible arm disposed on the first axial portion of the guide groove and a cantilevered lower flexible arm disposed on the second axial portion of the guide groove, and
wherein subsequent to the shield tab passing respective free ends thereof, the flexible arms prevent reverse displacement of the shield tab along the corresponding axial portions of the guide groove.

4. The injection device according to claim 3, wherein the upper flexible arm comprises a ramp at the free end thereof;
wherein as the shield tab passes the ramp, the shield tab radially displaces the free end of the upper flexible arm; and
wherein subsequent to the shield tab passing the ramp, the free end snaps back to form a portion of the helical portion of the guiding groove.

5. The injection device according to claim 3, wherein the lower flexible arm comprises a ramp at a free end thereof;
wherein as the biasing member completes the displacement of the medicament container to the withdrawn position, the shield tab travels in the second axial portion of the guiding groove and passes the ramp, radially displacing the free end of the lower flexible arm; and
wherein after the shield tab passes the ramp, the free end of the lower flexible arm snaps back to prevent displacement of the housing relative to the safety shield.

6. The injection device according to claim 3,
wherein the medicament container is slidably connected with the housing and the safety shield;

wherein the injector member comprises a plunger and a stopper disposed at a first end of the plunger, and the housing contacts a second end of the plunger opposite to the first end; and wherein displacement of the housing relative to the medicament container and the safety shield expels the medicament from the medicament container.

7. The injection device according to claim 6, wherein at the end of the stroke of the housing to expel medicament from the medicament container, the shield tab disposed on the shield engages the substantially helical portion of the guide groove; and upon release of the housing, the biasing member displaces the medicament container and the housing away from the safety shield, rotating the housing due to the engagement of the shield tab in the substantially helical portion.

8. The injection device according to claim 6, wherein the upper flexible arm comprises a locking protrusion selectively preventing displacement of the housing and the plunger relative to the medicament container;

wherein one of the upper flexible arm and the safety shield comprises an unlocking ramp and the remaining one of the upper flexible arm and the safety shield comprises a radial protrusion; and wherein upon displacement of the medicament container from the initial position to the injection position in which the needle extends beyond the safety shield, the unlocking ramp contacts the radial protrusion to radially displace a free end of the upper flexible arm, to permit movement of the housing relative to the medicament container.

9. The injection device according to claim 1, wherein upon the needle reaching a predetermined injection depth, the shield tab engages the substantially helical portion of the guide groove; and upon subsequent release of the injector member, as the biasing member displaces the housing and the medicament container, away from the safety shield, the housing rotates due to the engagement of the shield tab in the substantially helical portion of the guide groove.

10. The injection device according to claim 1, wherein:
the medicament container comprises a flexible blister;
the injector member comprises an injector button having an internal slot axially aligned with the flexible blister; and
as the injector button is depressed, the walls of the internal slot compress the flexible blister to expel the medicament from the medicament container.

11. An injection device, comprising:
a safety shield having a first end and a surface disposed at a second end thereof for contacting a patient's skin;
a medicament container slidably connected to the safety shield, the medicament container including a needle affixed thereto in communication with a medicament disposed within the medicament container, wherein the medicament container is displaceable relative to the safety shield from an initial position to an injection position, to a withdrawn position; an injector member comprising a plunger and a stopper disposed at a first end of the plunger;
a biasing member biasing the medicament container away from the safety shield; and
a housing slidably disposed with respect to both the safety shield and the medicament container, wherein the housing includes a cantilevered upper locking arm selectively preventing displacement of the housing and the plunger relative to the medicament container;

wherein one of the upper locking arm and the safety shield comprises a ramp and the remaining one of the upper locking arm and the safety shield comprises a corresponding radial protrusion;

wherein upon displacement of the medicament container from the initial position to the injection position in which the needle extends beyond the safety shield, the ramp contacts the radial protrusion to radially displace a free end of the upper locking arm, to permit movement of the housing relative to the medicament container;

wherein the housing contacts a second end of the plunger opposite to the first end; and wherein subsequent to the displacement of the medicament container from the initial position to the injection position, displacement of the housing relative to the medicament container and the safety shield expels the medicament from the medicament container.

12. The injection device according to claim 11, wherein the safety shield includes a depth stop for limiting penetration of the needle into a patient's skin.

13. An injection device, comprising:
a safety shield having a surface for contacting a patient's skin;
an inner housing slidably connected to the safety shield and having a cam track with first and second portions;
a needle hub slidably connected to the inner housing to move from a first position to a second position relative thereto;
a double-ended needle affixed to the needle hub;
a medicament container for holding a medicament, slidably connected to the safety shield;
a stopper slidably disposed in the medicament container;
a biasing member disposed within the safety shield and biasing the medicament container in a first direction; and
a needle shield for selectively covering a first end of the needle, the needle shield having at least one cam tab slidably engaged with the cam track;
wherein displacement of the cam tab along the first portion of the cam track displaces the needle hub to the second position, piercing the stopper with the needle.

14. The injection device according to claim 13, wherein displacement of the cam tabs along the second portion of the cam track removes the needle shield, readying the device for injection.

15. The injection device according to claim 14, wherein the combination of a back pressure of the medicament container and a friction between the stopper and the medicament container is greater than the combination of a force from the biasing member and a force required for the needle to pierce a patient's skin, so that upon displacement of the medicament container toward the patient's skin, the needle pierces the patient's skin prior to dispensing of the medicament.

16. The injection device according to claim 15, further comprising at least one locking tab biased toward deployment, wherein subsequent to completion of the injection, upon release of the medicament container, the biasing member displaces the medicament container and the inner housing in the first direction past the locking tab, and the locking tab deploys to prevent distal displacement of the inner housing therepast in a second direction opposite to the first direction.

17. The injection device according to claim 13, wherein the first portion of the cam track is substantially helical and the second portion of the cam track is substantially linear.

\* \* \* \* \*